United States Patent
Hofbauer et al.

(10) Patent No.: US 9,028,820 B2
(45) Date of Patent: May 12, 2015

(54) ANTIBODIES AGAINST TROPOMYOSIN-RELATED KINASE B RECEPTORS

(75) Inventors: Karl Hofbauer, Basel (CH); Jean-Christophe Peter, Ammerschwihr (FR)

(73) Assignee: University of Basel, Basel (CH)

( * ) Notice: Subject to any disclaimer, the term of this patent is extended or adjusted under 35 U.S.C. 154(b) by 0 days.

(21) Appl. No.: 14/116,186

(22) PCT Filed: May 18, 2012

(86) PCT No.: PCT/EP2012/059253
§ 371 (c)(1),
(2), (4) Date: Dec. 19, 2013

(87) PCT Pub. No.: WO2012/156505
PCT Pub. Date: Nov. 22, 2012

(65) Prior Publication Data
US 2014/0112928 A1    Apr. 24, 2014

(30) Foreign Application Priority Data
May 18, 2011 (GB) .................................. 1108296.3

(51) Int. Cl.
*C07K 16/28* (2006.01)
*A61K 39/395* (2006.01)
*C12N 5/16* (2006.01)
*A61K 39/00* (2006.01)

(52) U.S. Cl.
CPC ........... *C07K 16/28* (2013.01); *A61K 2039/505* (2013.01); *C07K 16/2863* (2013.01); *C07K 2317/34* (2013.01); *C07K 2317/55* (2013.01); *C07K 2317/622* (2013.01); *C07K 2317/76* (2013.01); *C07K 2317/77* (2013.01)

(58) Field of Classification Search
CPC ............... C07K 16/2863; C07K 16/28; C07K 2317/55; C07K 2317/622; A61K 39/39533; A61K 39/395; A61K 2039/505; C12N 5/16
See application file for complete search history.

(56) References Cited

U.S. PATENT DOCUMENTS 6,875,433 B2 * 4/2005 Hart et al. .................. 424/159.1
8,603,478 B2 * 12/2013 Whalen et al. ............. 424/133.1

FOREIGN PATENT DOCUMENTS

| WO | 2006/133164 | 12/2006 |
|---|---|---|
| WO | 2007/088476 | 8/2007 |
| WO | 2008/020827 | 2/2008 |
| WO | 2008/058127 | 5/2008 |
| WO | 2009/103538 | 8/2009 |

OTHER PUBLICATIONS

International Search Report issued Aug. 8, 2012 in International (PCT) Application No. PCT/EP2012/059253.
Cazorla et al., "Pharmacological characterization of six trkB antibodies reveals a novel class of functional agents for the study of the BDNF receptor", British Journal of Pharmacology, vol. 162, 2011, pp. 947-960.
R&D Systems, "Monoclonal Anti-human TrkB Antibody", R&D Systems Ordering Information, Catalog No. MAB397, Sep. 7, 2003.
R&D Systems, "Monoclonal Anti-mouse TrkB Antibody", R&D Systems Ordering Information, Catalog No. MAB1494, Dec. 21, 2004.
Ultsch et al., "Crystal Structures of the Neurotrophin-binding Domain of TrkA, TrkB and TrkC", Journal of Molecular Biology, vol. 290, 1999, pp. 149-159.
Banfield et al., "Specificity in Trk Receptor:Neurotrophin Interactions: The Crystal Structure of TrkB-d5 in Complex with Neurotrophin-4/5", Structure, vol. 9, Dec. 2001, pp. 1191-1199.
Bariohay et al., "Brain-Derived Neurotrophic Factor/ Tropomyosin-Related Kinase Receptor Type B Signaling is a Downstream Effector of the Brainstem Melanocortin System in Food Intake Control", Endocrinology, vol. 150, No. 6, Jun. 2009, pp. 2646-2653.
Hu et al., "BDNF heightens the sensitivity of motor neurons to excitotoxic insults through activation of TrkB", Journal of Neurochemistry, vol. 84, 2003, pp. 1421-1430.
Lin et al., "Appetite Enhancement and Weight Gain by Peripheral Administration of TrkB Agonists in Non-Human Primates", Plos One, vol. 3, Issue 4, Apr. 2008, pp. 1-7.

* cited by examiner

*Primary Examiner* — Ruixiang Li
(74) *Attorney, Agent, or Firm* — Wenderoth, Lind & Ponack, L.L.P.

(57) ABSTRACT

The invention relates to monoclonal antibodies directed to a particular part of tropomyosin-related kinase B receptor (TrkB) and hybridoma cell lines producing these. Fragments of these antibodies, in particular fragments representing complementarity determining regions (CDRs), and proteins comprising these, are useful in a method of treating cancer, pain, anorexia, anorexia nervosa and/or cachexia.

18 Claims, 7 Drawing Sheets

ANTIBODIES AGAINST TROPOMYOSIN-RELATED KINASE B RECEPTORS

This application is a 371 of PCT/EP2012/059253, filed May 18, 2012, which claims foreign priority to United Kingdom 1108296.3, filed May 18, 2011.

FIELD OF THE INVENTION

The invention relates to monoclonal antibodies directed to a particular part of tropomyosin-related kinase B receptors (TrkB), hybridoma cell lines producing these, fragments of the antibodies and proteins comprising these, pharmaceutical compositions and a method of treating cancer, pain, anorexia and/or cachexia.

BACKGROUND OF THE INVENTION

Tropomyosin-related kinase receptors (Trk) are activated by neurotrophins including nerve growth factor (NGF), brain-derived neurotrophic factor (BDNF), neurotrophin 3 and 4/5 (NT3, NT4/5). Trk regulates neuronal development, survival differentiation and synaptic plasticity (Nikoletopoulou V. et al., 2010, *Nature* 467:59-63; Chao M. V., 2003, *Nat Rev Neurosci* 4:299-309). Neurotrophins initiate their cellular responses by binding their specific Trk subtypes. NGF is specific for TrkA, whereas BDNF and NT4/5 are specific for TrkB. NT3 primarily activates TrkC but also other Trk with less efficiency. Neurotrophins binding to Trk induces Trk dimerization and autophosphorylation at specific tyrosine residues in the cytoplasmic domain. This creates docking sites for adaptor proteins that activate PI3K/Akt, MEK/ERK, and PLCγ signaling pathways (Huang E. J. and Reichardt L. F., 2003, *Annu Rev Biochem* 72:609-642). Formation of Trk/neurotrophin complex also initiates endocytosis required for some biological functions of neurotrophins (Grimes M. L. et al., 1996, *J Neurosci* 16:7950-7964; Zheng J. et al., 2008, *J Biol Chem* 283:13280-132).

TrkB and its endogenous ligand BDNF are also important components for the regulation of energy balance and eating behavior in mammals. In previous studies we and other authors have demonstrated that BDNF and its TrkB are downstream mediators of the MC4R (Xu B. et al., 2003, *Nat Neurosci* 6:736-742; Nicholson J. R. et al., 2007, *J Neuroendocrinol* 19:974-982; Bariohay B. et al., 2009, *Endocrinology* 150:2646-2653). In humans, genetic dysfunction of either TrkB or MC4R leads to hyperphagia and obesity (Yeo G. S. et al., 2004, *Nat Neurosci* 7:1187-1189).

ScFv antibody fragments represent the next generation of biologics (Kontermann R. E., 2010, *Curr Opin Mol Ther* 176-183). Due to their small size compared with the whole antibody, they are able to cross the blood/brain barrier (Peter J. C. et al., 2010, *J Pharmacol Exp Ther* 478-490).

SUMMARY OF THE INVENTION

The invention relates to a monoclonal antibody directed against a peptide consisting of at least 14 amino acids and maximum 50 amino acids selected in sequence from residues 252 to 322 of TrkB of SEQ ID NO:1, comprising Asp-298 and Cys-302, in particular such an antibody against the B1 peptide of SEQ ID NO:2. Furthermore the invention relates to hybridoma cell lines producing antibodies of the invention, in particular the cell lines 5G5D2B5 and 6B72C5. Furthermore, the invention relates to fragments of the antibodies of the invention, such as Fab fragments, scFv fragments and CDRs, proteins comprising such CDRs, and pharmaceutical compositions comprising these. The invention further relates to a method of treating cancer, pain, anorexia and/or cachexia comprising administering a therapeutically efficient amount of an antibody fragment of the invention and of proteins comprising these.

BRIEF DESCRIPTION OF THE FIGURES

FIG. 1:

a. Delta body weight evolution of rats immunized with the B1 peptide which developed anti-TrkB antibodies (Abs), control rats immunized with CO peptide and sham immunized rats. -■- sham (n=10); -▲- control (CO peptide, n=10); ---▼--- TrkB (B1 peptide, n=12); x-axis d=days post immunization; y-axis Δ(g)=delta body weight in g. Rats immunized with B1 peptide showed a significant (*:p<0.05, two-way ANOVA) gradual increase in their body weight as compared with the two controls groups.

b. Glucose tolerance test and insulin tolerance test of the rats immunized with the B1 peptide. The panels represent the glycemia of rats with received an i.p. bolus of glucose (glucose tolerance test, left panel) or insulin (insulin tolerance test, right panel). No difference has been detected between control and B1 immunized rats.

x-axis min=minutes post immunization; y-axis Δ(mM)= delta glucose ($T_n$-$T_0$) in mM.

c. Cumulative food intake of rats immunized with the B1 peptide and control rats which received an i.p. injection of LPS (75 μg/kg). Rat immunized with B1 peptide showed a significant early resistance to the LPS induced anorexia as compared with control rats (*:p<0.05, two-way ANOVA with repeated measures).

x-axis h=hours after LPS injection; y-axis g=cumulative food intake; left bar (grey) CO (n=10); right bar (black) TrkB (n=12).

FIG. 2:

Purified anti-TrkB Abs bind the native form of TrkB a. Immunoprecipitation experiments.

b. Inhibition ELISA confirmed the specificity of the binding for B1 peptide and TrkB. C=control; % I=% inhibition (y axis); Log [I] (M)=Log [inhibitor], concentration in Mol (x axis); -■- B1 peptide; -▲- recombinant TrkB.

FIG. 3:

a. Concentration-response curves obtained with purified anti-TrkB (---▼---) and control Abs (-▲-) on PC12 cells (left panel) or neurons prepared form ES cells (right panel). -■-: PBS only. Y-axis: %=Phospho-TrkB (% from maximum). The presence of 10 nM of rat anti-TrkB Abs decreased maximum efficacy while control Abs had no effect.

b. Concentration-response curves obtained with purified anti-TrkB Abs and anti-TrkB Fab on PC12 cells. The presence of 10 nM of rat anti-TrkB Fab (---▲---) decreased maximum efficacy. -■-: PBS only. Results are expressed as percentage of maximum phosphorylation. Results are presented as mean±SD; , p<0.01; *, p<0.001, F-test. y axis: % TrkB phosphorylation; x axis: Log [BDNF] in Mol

FIG. 4:

Western blot of PC12-TrkB cells extract treated with (Black bars) or without BDNF (White bars) in presence (Dashed bars) or absence of anti-TrkB Abs. The presence of anti-TrkB Abs increased the internalization alone or induced by BDNF. Results are expressed as average percentage of internalization (% I)±SD; ** p<0.01, Student's t-test.

FIG. 5:

Concentration-response curves obtained with purified anti-TrkB (---▲---) and control Abs (-■-) on PC12 cells. The presence of 10 nM of rat anti-TrkB Abs decreased maximum efficacy of PLCγ phosphorylation (% P) while control Abs had no effect. Results are expressed as mean±SD; *, p<0.05, Student's t-test. x axis: Log [BDNF] in Mol, y axis: % TrkB phosphorylation

FIG. 6:

a. Cumulative food intake (FI) of rats which received 1 µg of anti-TrkB Abs or control Abs intracerebroventriculary (i.c.v.) in the third ventricule. b., c. and d. represent, respectively, the cumulative FI during the $1^{st}$, $2^{nd}$ and $3^{rd}$ 24 h after i.c.v. injection. The i.c.v. injection of TrkB Abs increased food intake compared to control Abs (lower line). Data presented as mean±sem. *, p<0.05, **:p<0.01, two way Anova test. Y-axis: Cumulative food intake in g; x-axis: h=time in hours.

FIG. 7:

a. & b. Concentration-response curves obtained with purified anti-TrkB mAb 5G5D2B5 and anti-TrkB scFv 5G5D2B5 in PC12 cells.

y-axis: %=Phospho-TrkB (% from maximum). The presence of 30 nM of rat anti-TrkB mAb 5G5D2B5 (a. (---▼---)) or 300 nM of scFv 5G5D2B5 (300 nM) (b. (---▼---)) decreased maximum efficacy. -■-: PBS only. Results are expressed as percentage of maximum phosphorylation, **:p<0.01 F-test. x-axis: Log [BDNF] (M).

c. Internalization of TrkB studied by Western blot of PC12-TrkB cell extracts treated with or without BDNF in the presence or absence of scFv 5G5D2B5 or anti-TrkB Abs. The presence of scFv 5G5D2B5 increased the internalization induced by BDNF. Results are expressed as average percentage of internalization (% I)±SD; , p<0.01; *, p<0.001, one-way ANOVA.

FIG. 8:

a. 7-days cumulative food intake (FI) in rats which received 1 µg of scFv 5G5D2B5 (upper curve) (n=9) or BSA (lower curve) (n=7) i.c.v. into the third ventricle. The injection of scFv 5G5D2B5 increased FI compared to controls. h=time in hours.

b. Body weight change in g (y-axis) during 7 days after i.c.v. administration of scFv 5G5D2B5 or BSA as control. scFv 5G5D2B5 (---▲---) induced an increase in body weight compared with rats which received BSA (-■-). Data presented as mean±sem. *:p<0.05, two-way ANOVA Bon Ferroni post-hoc test. d=time in days.

DETAILED DESCRIPTION OF THE INVENTION

The invention relates to monoclonal antibodies directed against a peptide consisting of at least 14 amino acids and maximum 50 amino acids selected in sequence from residues 252 to 322 (d5 domain of the TrkB receptor) of TrkB of SEQ ID NO:1, comprising Asp-298 and Cys-302.

Preferred are monoclonal antibodies directed against a peptide consisting of at least 16 amino acids and maximum 25 amino acids selected in sequence from residues 280 to 320 of TrkB of SEQ ID NO:1, comprising Asp-298 and Cys-302.

Most preferred are monoclonal antibodies against B1 peptide,

```
       TITFLESPTSDHHWCIPFTV,       (SEQ ID NO: 2)
``` residues 288-307 of TrkB (SEQ ID NO:1), in particular the monoclonal antibody produced by hybridoma cell line 5G5D2B5 and by hybridoma cell line 6B72C5 deposited at the Deutsche Sammlung für Mikroorganismen and Zellkulturen, Inhoffenstr, 7 B, D-38124 Braunschweig, Germany (German Collection of Microorganisms and Cell Cultures, DSMZ) under the numbers DSM ACC3124 and DSM ACC3125, respectively, on Apr. 15, 2011.

Likewise the invention relates to hybridoma cells producing monoclonal antibodies directed against a peptide consisting of at least 14 amino acids and maximum 50 amino acids selected in sequence from residues 252 to 322 of TrkB of SEQ ID NO:1, comprising Asp-298 and Cys-302.

Preferred are hybridoma cells producing monoclonal antibodies directed against a peptide consisting of at least 16 amino acids and maximum 25 amino acids selected in sequence from residues 280 to 320 of TrkB of SEQ ID NO:1, comprising Asp-298 and Cys-302.

Most preferred are hybridoma cells producing monoclonal antibodies against B1 peptide (SEQ ID NO:2), in particular the hybridoma cell line 5G5D2B5 and the hybridoma cell line 6B72C5 deposited at DSMZ under the numbers DSM ACC3124 and DSM ACC3125, respectively, on Apr. 15, 2011.

Furthermore the invention relates to fragments of the mentioned antibodies. Fragments considered are Fab and scFv fragments and proteins representing complementarity determining regions (CDRs), for example the CDRs of the monoclonal antibody named mAb 6B72C5:

```
CDR L1:    CSLSSQHSTYTIE;         (SEQ ID NO: 3)

CDR L2:    LKKDGSH;               (SEQ ID NO: 4)

CDR L3:    CGVGDTIKEQFVYV;        (SEQ ID NO: 5)

CDR H1:    SGFNIKDTYMH;           (SEQ ID NO: 6)

CDR H2:    IDPAHNNIKYDPKFQGK;     (SEQ ID NO: 7)

CDR H3:    CTGSLGRGDYF;           (SEQ ID NO: 8)
``` and the CDRs of the monoclonal antibody named mAb 5G5D2B5:

```
CDR L1:    CRSSTGAVTTSNYAS;       (SEQ ID NO: 9)

CDR L2:    GGTNNRA;               (SEQ ID NO: 10)

CDR L3:    CALCYSNHLV;            (SEQ ID NO: 11)

CDR H1:    SGFTFSNYAMS;           (SEQ ID NO: 12)

CDR H2:    ISSGGSTYYPDSVKGR;      (SEQ ID NO: 13)

CDR H3:    CARGRGLRLRSYYYALDY;    (SEQ ID NO: 14)
``` and proteins comprising these mentioned CDRs of SEQ ID NO: 3 to 14.

For the manufacture of monoclonal antibodies, standard methods may be used. Preferably Balb/C mice are immunized with the free B1 peptide emulsified in complete Freund's adjuvant and injected subcutaneously (s.c.) in amounts of 10 to 40 µg, for example 25 µg, followed by a booster injection of the same amount of free B1 peptide in incomplete Freund's adjuvant after two to five weeks, for example four weeks. Another two to five weeks later a smaller amount, e.g. 10 µg, peptide without adjuvant (dissolved in NaCl 0.9%) is injected i.v. three days before harvesting the spleen cells for fusion.

Fusion is preferably performed with polyethylene glycol, such as polyethylene glycol 1500, or the Sendai virus with a myeloma cell lacking the hypoxanthine-guanine phosphoribosyl-transferase (HGPRT gene), for example the SP2O cell, preferably at a ratio of 2 splenocytes for 1 SP2/O myeloma cell. Hybridomas are cultivated in 96 well plates precoated with murine peritoneal macrophages or other feeder cells. $10^5$ to $10^6$ fused cells are distributed per well in Isocoves Modified Dulbecco's Medium (IMDM) supplemented with heat inactivated fetal calf serum, glutamine, odium pyruvate, penicillin and/or streptomycin, and HAT (Hypoxanthine, Aminopterine, Thymidine) or an equivalent medium comprising HAT in a humidified incubator at 37° C. under an atmosphere of 5% $CO_2$. Secreting clones are screened by enzyme immunoassay and subcloned by limiting dilution.

The manufacture of scFvs can likewise be performed using standard methods. For example, total RNA is prepared from around $10^7$ freshly subcloned hybridoma cells using the RNAnow kit (Biogentex Inc., Seabrook, Tex., USA). A first strand cDNA may be synthesized using iScript™ cDNA Synthesis kit (Biorad, Hercules, Calif., USA). The $V_H$ and $V_L$ chain domains are amplified by PCR using an IgG primer set (Novagen, Gibbstown, N.J., USA). scFv proteins are created by joining their $V_H$ and $V_L$ genes together by PCR splicing with overlap extensions using oligo-nucleotides that encode a 15 amino-acid linker $(G_4\text{-}S)_3$ between the C-terminal of the $V_H$ and the N-terminal of the $V_L$ gene.

Furthermore the invention relates to graft of CDRs mentioned above on a human antibody framework or human scFv framework.

Furthermore the invention relates to pharmaceutical compositions comprising the antibody fragments. Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described. The scFv Ab of the present invention can be provided as a synthetic peptide or an isolated and substantially purified protein or protein fragments or a combination thereof in pharmaceutically acceptable compositions using formulation methods known to those of ordinary skill in the art. These compositions can be administered by standard routes.

Furthermore the invention relates to a method of treating cancer, pain, cachexia or anorexia nervosa comprising administering a therapeutically efficient amount of an antibody fragment of this invention to a patient in need thereof.

Examples of cancer to be treated include cancer of neural system, neuroblastoma, Wilm's tumours, glial tumours, myeloma, Kaposi's sarcoma, leukemias, melanoma, prostate adenocarcinomas, and liver and pancreatic adenocarcinomas. The invention likewise relates to treating cancer by suppressing angiogenesis, tumour formation and metastasis.

In embodiments of pain treatment, the pain is associated with neuropathic pain and/or CNS dysfunction. In a further embodiment, pain may be neuropathic pain, somatic or visceral pain. For example, the neuropathic pain may be associated with a nerve or tract injury. In yet another embodiment, pain may be chronic inflammatory pain, pain associated with arthritis, fibromyalgia, back pain, cancer-associated pain, pain associated with digestive disease, pain associated with Crohn's disease, pain associated with autoimmune disease, pain associated with endocrine disease, pain associated with diabetic neuropathy, phantom limb pain, spontaneous pain, chronic post-surgical pain, chronic temporomandibular pain, causalgia, post-herpetic neuralgia, AIDS-related pain, complex regional pain syndromes type I and II, trigeminal neuralgia, chronic back pain, and pain associated with spinal cord injury or recurrent acute pain.

Cachexia and anorexia nervosa are life-threatening diseases characterized by severe loss of body weight. Cachexia is caused by various underlying disorders, such as cancer, inflammation or infections but is an independent risk factor for morbidity and mortality. Anorexia nervosa is a psychiatric disease in which weight loss is caused by the patients' deliberate refusal to eat despite strong feelings of hunger. The negative energy balance of these patients is often enhanced by increased physical activity.

Likewise the invention relates to an antibody fragment for use in the treatment of cancer, pain, cachexia or anorexia nervosa, and to the use of an antibody fragment of the invention for the manufacture of a pharmaceutical composition for the treatment of cancer, pain, cachexia or anorexia nervosa.

The scientific rationale is as follows:

Rats were immunized against a peptide derived from an extracellular loop of TrkB which is responsible for the specificity of the interaction of the TrkB with its endogenous ligand BDNF. Rats immunized with this peptide developed specific Abs which were purified and evaluated in a series of in vitro experiments using PC12 cells expressing TrkB or neurons prepared from mouse ES cells. Rats which developed anti-TrkB Abs showed a gradual increase in body weight during the time course of the experiments compatible with a blockade of TrkB. An increased food intake was observed after central administration of the purified anti-TrkB Abs in rats.

Immunization of rats resulted in a mild phenotype compatible with a TrkB blockade without any apparent neurological effects. Because of the efficacy of the Abs on TrkB activity demonstrated in vitro as well as in vivo, these Abs can be used as pharmacological tools and modified for use as therapeutic agents.

Figure 1:
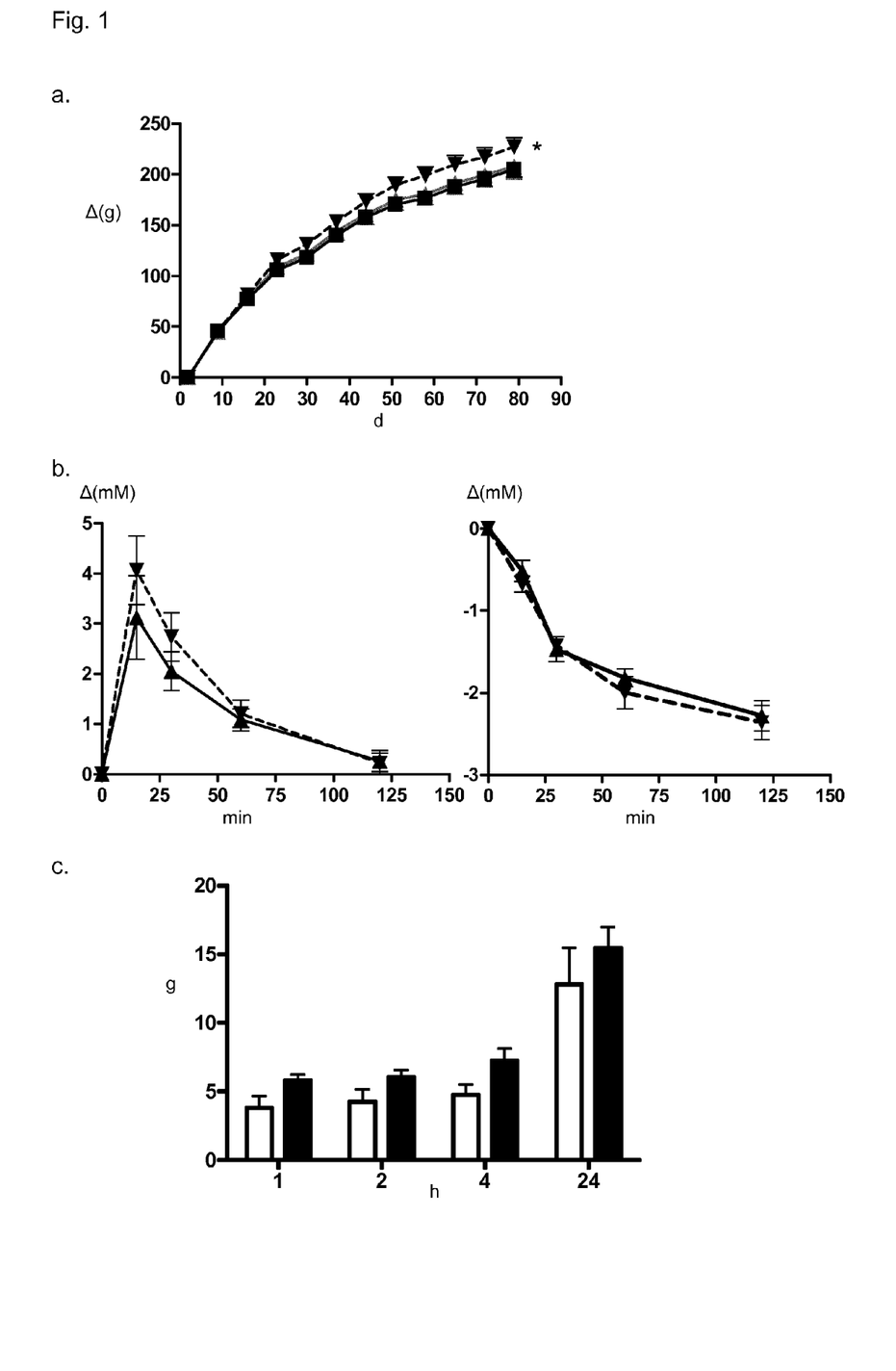

Rats which developed anti-TrkB Abs gradually and significantly increased their body weight as compared to control rats (FIG. 1a, $p<0.05$, two-way ANOVA with repeated measures, Bonferroni post-hoc test). Neither glucose tolerance nor insulin tolerance revealed significant changes in glucose metabolism of immunized rats (FIG. 1b). At day 80 post immunization, rats received an i.p. injection of lipoplysaccharides (LPS). Food intake of rats which developed anti-TrkB Abs was significantly higher ($p<0.05$, Two-way ANOVA with repeated measures) as compared with control rats (FIG. 1c). No differences in metabolites as well as in organ weights were found at the end of the experiments (Table I and II). Body weight and body weight/length ratio were higher in the TrkB immunized rats.

TABLE I

Plasma parameters of immunized rats against TrkB (TrkB), immunized rats against control peptide (CO) and Sham rats.

|  | TrkB (n = 12) | CO (n = 10) | Sham (n = 10) | Significance |
|---|---|---|---|---|
| Glucose (mM) | 7.1 ± 1.9 | 6.7 ± 1.7 | 7.3 ± 1.4 | n.s |
| Triglycerides (mM) | 0.6 ± 0.3 | 0.7 ± 0.3 | 0.6 ± 0.1 | n.s. |
| FFA (mM) | 0.3 ± 0.1 | 0.3 ± 0.1 | 0.3 ± 0.3 | n.s. |
| Insulin (ng/ml) | 0.6 ± 0.7 | 0.8 ± 0.8 | 0.6 ± 0.3 | n.s. |
| Leptin (ng/ml) | 2.6 ± 1.4 | 2.6 ± 1.6 | 2.0 ± 0.6 | n.s. |
| IL-6 (pg/ml) | 95.7 ± 49.5 | 114.6 ± 82.7 | 72.7 ± 137.5 | n.s. |
| TNFα (pg/ml) | 19.0 ± 34.4 | 19.7 ± 14.2 | 13.3 ± 16.6 | n.s. |

Mean ± SD,
n.s.: not significant.

TABLE II

Phenotype and organ weight of immunized rats against TrkB (TrkB), immunized rats against control peptide (CO) and Sham rats.

|  | TrkB (n = 12) | CO (n = 10) | Sham (n = 10) | Significance |
|---|---|---|---|---|
| Length (cm) | 46.9 ± 0.9 | 46.5 ± 1.4 | 47.2 ± 1.3 | n.s |
| Body weight (g) | 505 ± 44 | 490 ± 52 | 476 ± 27 | * |
| Heart (g) | 1.4 ± 0.1 | 1.4 ± 0.1 | 1.4 ± 0.1 | n.s. |
| Liver (g) | 14.1 ± 2.3 | 13.7 ± 2.4 | 12.8 ± 0.8 | n.s. |
| Fat pads (g) | 11.7 ± 4.4 | 10.4 ± 3.7 | 9.5 ± 2.4 | n.s. |
| BW/Length (g/cm) | 10.8 ± 0.8 | 10.5 ± 0.9 | 10.1 ± 0.4 | * |

Mean ± SD,
*: p < 0.05, Student's t-test vs. Sham.

Figure 2:
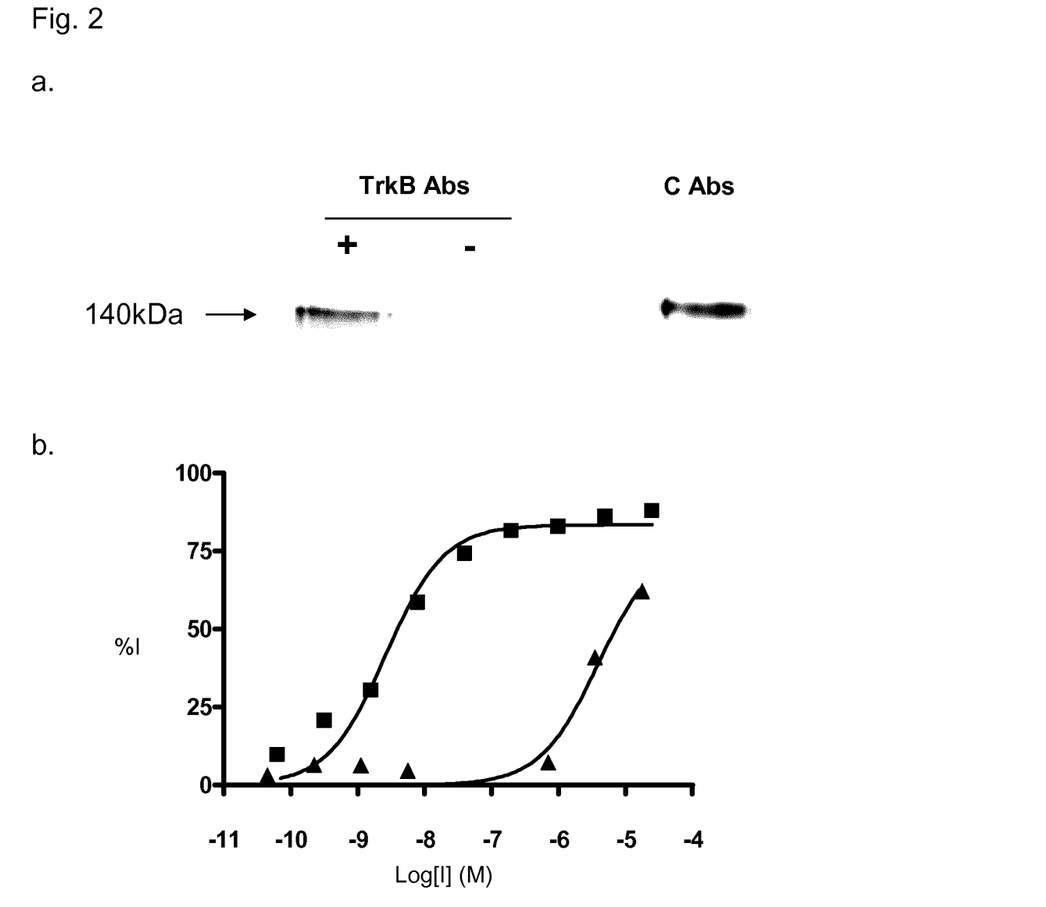

The selectivity of the Abs was studied by immunocytofluorescence, immunoprecipitation and inhibition ELISA. Immunoprecipitation using membrane preparation from PC12-cells demonstrated the interaction between anti-TrkB Abs and TrkB (FIG. 2a). Inhibition ELISA confirmed this interaction and showed that anti-TrkB Abs have apparently 1000 times higher affinity for the B1 peptide than for TrkB (FIG. 2b)

Figure 3:
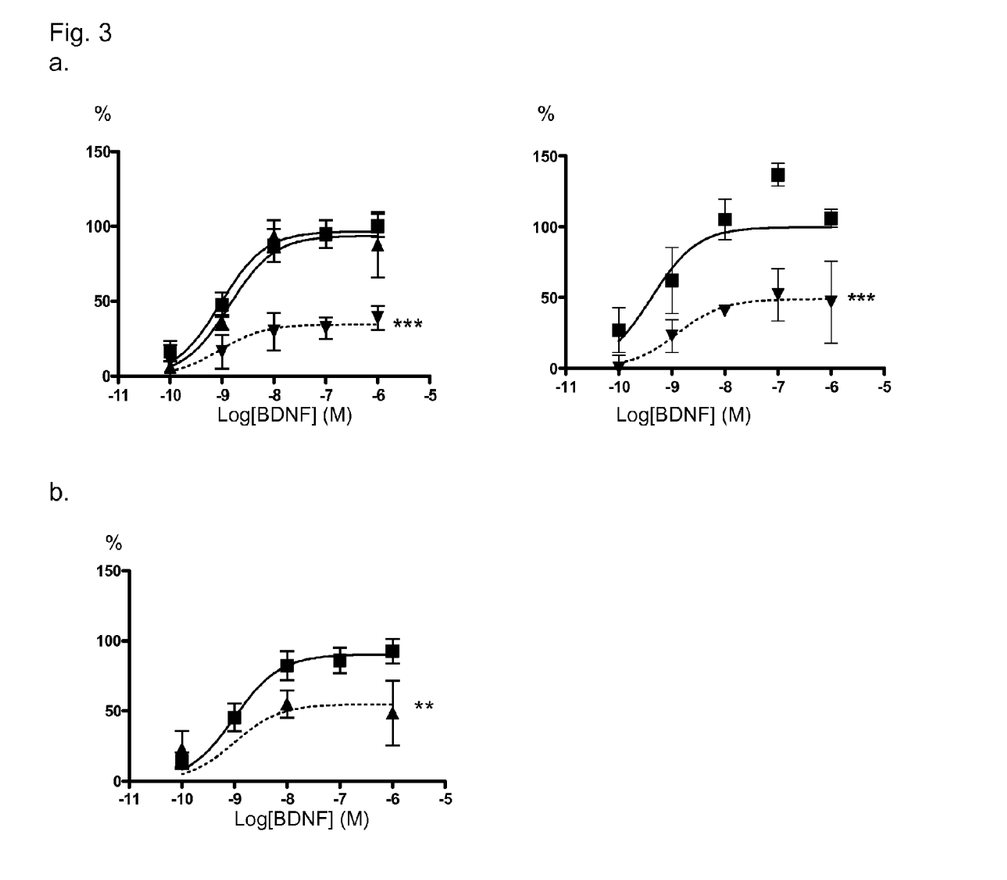

The pharmacological activity of the anti-TrkB Abs was studied in PC12 cells expressing TrkB and in neurons prepared from mouse ES cells. In these experiments, cells were treated with increasing concentrations of BDNF in presence or in absence of anti-TrkB Abs. The phosphorylation of TrkB which reflects its activation was studied by Western blot experiments (FIG. 3a). In presence of 10 nM of anti-TrkB Abs, the maximum effect of BDNF on TrkB phosphorylation was significantly decreased in both cell types ($p<0.001$, F-test; FIG. 3b). The presence of anti-CO Abs did not influence the maximum effect. Moreover Fab fragment prepared from purified anti-TrkB Abs had the same effect on PC12 cells (FIG. 3c).

Figure 4:
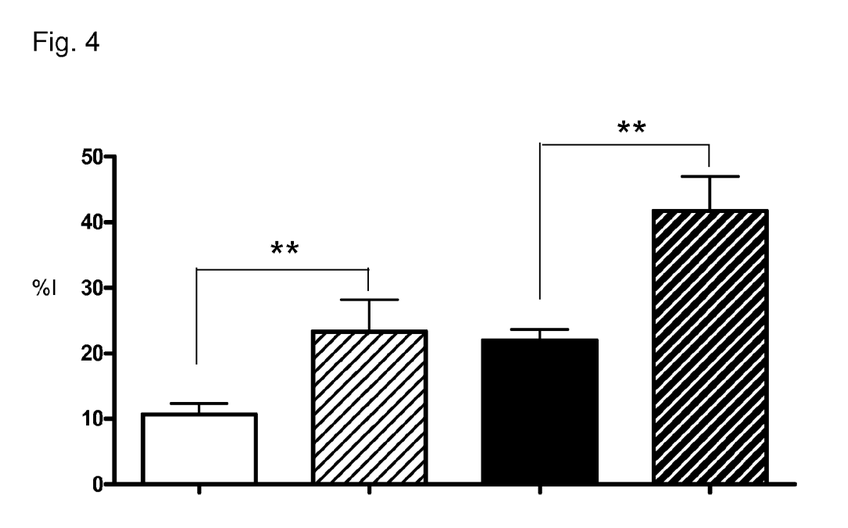

Internalization of TrkB was studied in PC12 cell expressing TrkB. A treatment of BDNF increased the internalization of TrkB (FIG. 4). The presence of anti-TrkB Abs induced a 50% increase in the basal internalization of TrkB and internalization in the presence of BDNF (FIG. 4).

Figure 5:
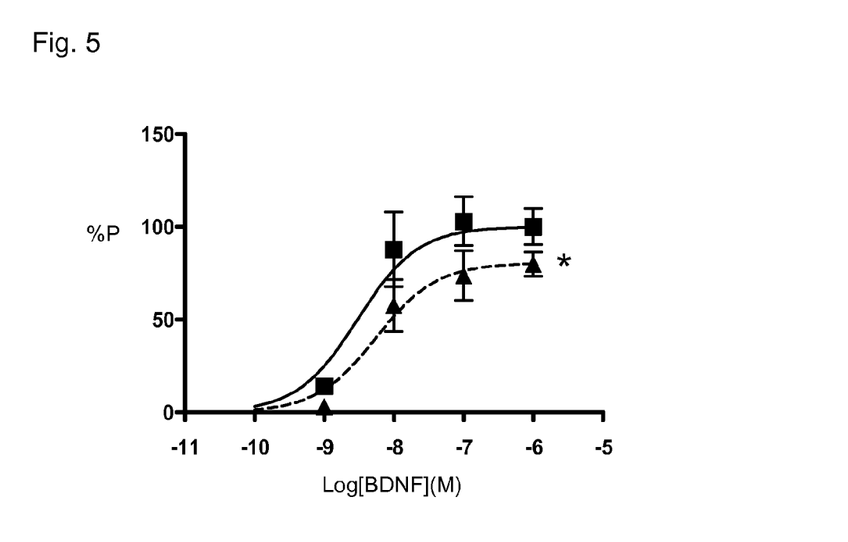

The effect of anti-TrkB Abs on the TrkB signaling pathway was studied to confirm the downstream effects of a TrkB blockade. The presence of the anti-TrkB Abs induced a significant decrease in the maximum activation of PLCγ phosphorylation upon treatment of PC12 cell with increasing concentrations of BDNF (FIG. 5).

Figure 6:
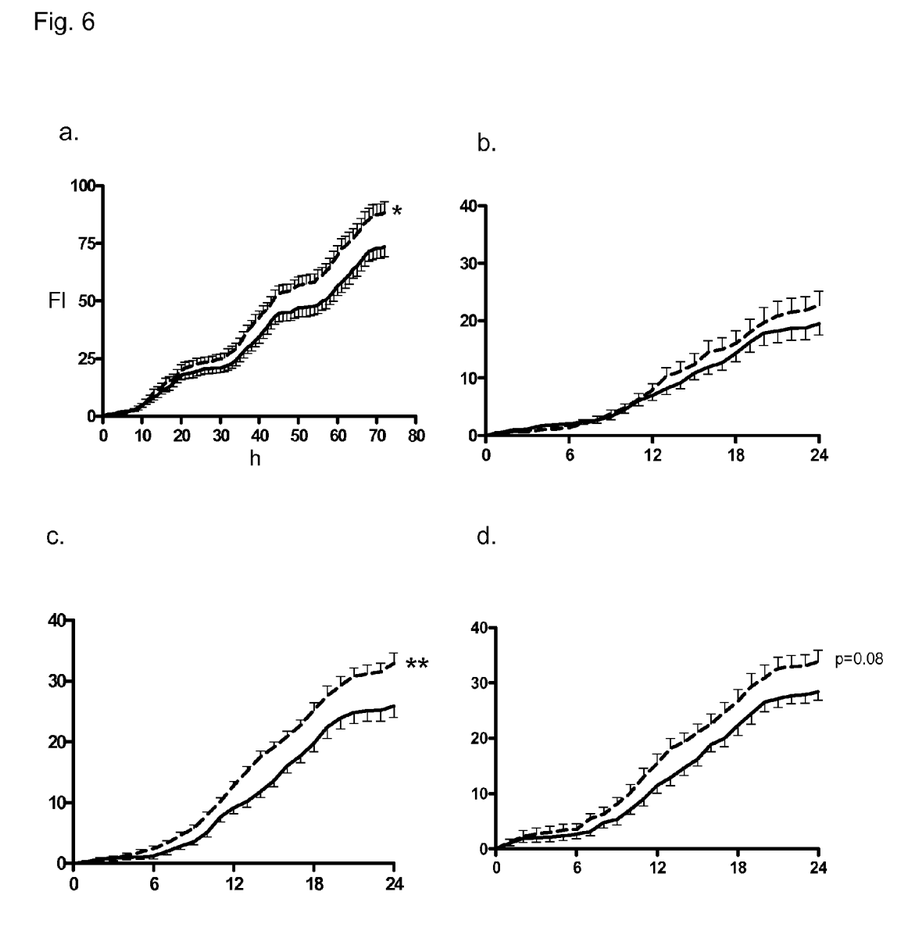
Figure 7:
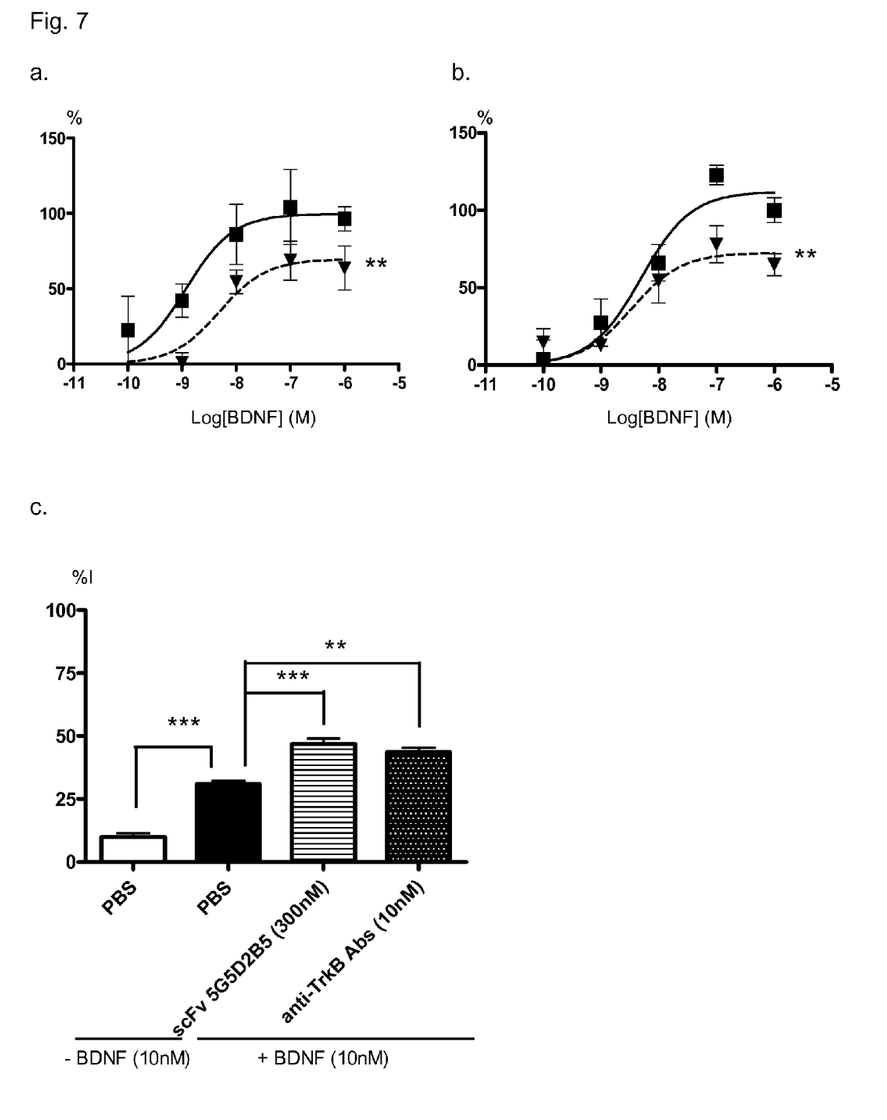
Figure 8:
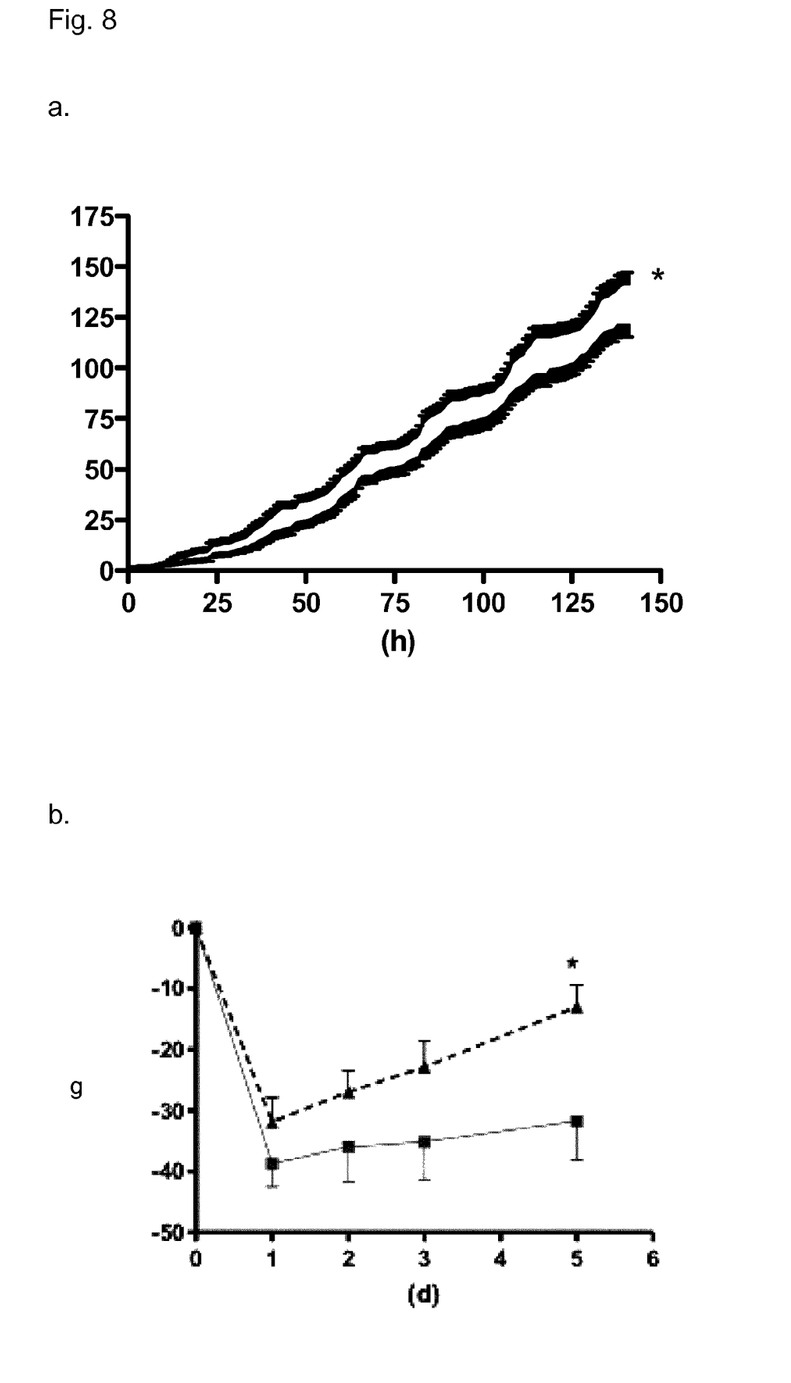

Purified anti-TrkB Abs or anti-CO Abs (1 μg) were injected into the third ventricle of rats. Rats which received anti-TrkB Abs showed a significant increase in food intake over 72 h as compared with control rats ($p<0.05$, two-way ANOVA with repeated measures, FIG. 6a). The effect was moderate over the first 24 h (+15%) but became stronger (+28%) and significant ($p<0.01$, two-way ANOVA with repeated measures) over the second 24 h period after injection (FIG. 6b, c). After the third 24 h the effect appeared to be still present (+19%) but was no longer significant (FIG. 6d). No side effects (neurological disturbances) were observed in these rats.

These results demonstrate that pharmacologically active Abs can be generated against TrkB which is part of the downstream pathway of the MC4R. The selection of a suitable target peptide used as antigen is a prerequisite for a successful immunization. From the crystal structure of the D5 domain of TrkB receptor a loop corresponding to the putative binding site of NT4/BDNF was selected. By inducing a humoral immune response against this extracellular loop, the induced Abs block the access of the neurotrophin and therefore block TrkB receptor activation.

The peptide was injected in complete Freund's adjuvant without coupling to a carrier protein.

The properties of anti-TrkB Abs were evaluated in a series of in vitro experiments after purification with immunoadsorption of the B1 peptide. Immunochemistry experiments in PC12 cells expressing the human TrkB, immunoprecipitation experiments or inhibition ELISA demonstrated the specific binding of the Abs to TrkB. The apparent affinity of the Abs seemed to be lower for the TrkB as compared with peptide B1. This is probably due to a lower accessibility of the binding site in the receptor as compared with the peptide.

In the experiments on PC12 cells expressing TrkB, the presence of anti-TrkB Abs decreased the maximum efficacy of BDNF on TrkB phosphorylation. This pharmacological profile was confirmed in neurons prepared from mouse ES cells. Anti-TrkB Abs triggered the internalization of the receptor and thereby limited the exposure of the receptor to BDNF. Internalization experiments showed that the presence of anti-TrkB Abs doubled the basal and the BDNF induced internalization by a factor 2.

Anti-TrkB Abs have agonist properties on the receptor and induced its internalization. Monovalent Fab fragments were produced which have the same blocking properties than the whole molecule. Moreover, PLCγ phosphorylation upon BDNF treatment was studied on PC12 cell in presence or in absence of anti-TrkB Abs. The same decrease of the maximum efficacy of BDNF on PLCγ phosphorylation was observed which confirmed a blockade of TrkB. Taken together, these informations indicate that the phenomenon of internalization observed is not due to an activation of the receptor in response to dimerization and that the global cellular response is a decreased efficacy of PLCγ.

After immunization, rats developed anti-TrkB Abs and showed a gradual increase in body weight. Rats which developed anti-TrkB Abs did not show any disturbance of their glucose metabolism, as neither glucose tolerance test nor insulin tolerance test showed any differences as compared with control rats. Moreover, no differences in organ weights were detected. Only body weight increased in these rats as compared with controls.

When LPS was injected in rats that had been actively immunized against TrkB, the decrease in food intake was partially prevented. These results indicate that anti-TrkB Abs confer significant protection against the LPS-induced anorexia. Taking into account that BDNF is released after an MC4R stimulation, these observations are consistent with reports that have demonstrated that MC4R blockade by pharmacologic means or by genetic manipulation has a protective effect in the LPS model.

Taken together, these experiments demonstrated that immunization of rats with a TrkB peptide resulted in a phenotype with increased body weight. Purified anti-TrkB Abs were characterized in vitro as blockers of TrkB which acted by enhancing their internalization. Passive transfer of purified Abs induced an increase in food intake. The predominant effect of acute or chronic TrkB blockade appears to be the induction of a positive energy balance. Such Abs and derivatives thereof can therefore be used to treat anorexia and cachexia.

EXAMPLES

Peptide

A peptide corresponding to the first loop of the D5 domain of the TrkB (Banfield M. J. et al., *Structure* 9:1191-1199) (B1 peptide, TITFLESPTSDHHWCIPFTV (SEQ ID N0:2), residues 288-307) and control (CO) peptide (Peter J. C. et al., 2007, *Am J Physiol Regul Integr Comp Physiol* 292:R2151-2158) were synthesized (Neimark J. and Briand J. P., 1993, *Pept Res* 6:219-228).

Animals

Male Sprague-Dawley rats, 6 weeks old at the beginning of the experiments (initial body weight approximately 200 g), were obtained from Charles River (Charles River Laboratories, L'Arbresle, France), and kept at a 12 h light/dark cycle (lights on from 6:00 a.m. to 6:00 p.m.) in a room with constant temperature (22° C.) and humidity (50%). Rats were housed individually one week before the beginning of an experiment and were given free access to tap water and standard laboratory chow (NAFAG 3432, 3.0 kcal/g, 61.6% of total calories from carbohydrate, 24.8% from protein and 13.6% from fat, Nafag Ecosan, Switzerland). All experiments were performed in accordance with the Swiss regulations for animal experimentation.

Active Immunization in Rats

Rats were divided into 3 groups: a sham treated control group (sham, n=10), a group immunized with the B1 peptide (n=12) and a group immunized with the CO peptide (n=10). Peptides were applied subcutaneously (s.c.) behind the neck (25 µg peptide/rat in 0.2 ml complete Freund's adjuvant for the first injection). 30 and 60 days later rats received two booster injections of peptides in incomplete Freund's adjuvant. In order to estimate the efficacy of the immunization procedure, blood was collected before each injection by tail bleeding under isoflurane anesthesia, and the presence of anti-peptide antibodies (Abs) was assessed by ELISA test. Body weight and food intake were recorded once per week at 9:00 a.m. At the end of the experiments rats were killed by decapitation under isoflurane anesthesia and blood was collected in EDTA treated tubes.

Determination of the Immune Response by Direct ELISA

B1 and CO peptides (2 µM) were adsorbed with carbonate buffer ($Na_2CO_3$ 15 mM, $NaHCO_3$ 35 mM, pH 9.6), on 96-wells microtiter plates (BD Biosciences, San Jose, Calif., USA), 50 µl/well, by incubating for 1 h at 37° C. Plates were saturated with Phosphate Buffered Saline (PBS) ($Na_2HPO_4$ 10 mM, NaCl 150 mM, KCl 27 mM, pH 7.4) supplemented with 1% bovine serum albumin (BSA) (Sigma, St. Louis, Mo., USA), and 0.05% Tween 20 (Fluke, Buchs, Switzerland) (PBS-T BSA) for 1 h at room temperature (RT). Serial dilutions of rat sera were added to the plates and incubated for 1 h at RT. Plates were then washed with PBS containing 0.05% Tween 20 (PBS-T) and incubated with goat anti-rat immunoglobulin G (IgG) horseradish peroxidase conjugated (Jackson Immunoresearch Laboratories, San Diego, Calif., USA), diluted 1/5000, for 1 h at RT. After washing the plates with PBS-T and PBS, enzymatic reactions were carried out at RT by adding 3,3',5,5'-tetramethylbenzidine (TMB) in the presence of 0.04% $H_2O_2$. Reactions were stopped after 15 min by the addition of HCl (1 N). Optical density was measured at 450 nm by using a microplate reader Multiscan RC (Labsystem, Kilsyth, Victoria, Australia).

Inhibition ELISA

Purified TrkB Abs were pre-incubated with increasing concentrations ($2\times10^{-12}$ to $2\times10^{-6}$ M) of the B1 peptide or the recombinant TrkB in solution. The mixture was submitted to the standard ELISA procedure (Peter J. C. et al., 2007, *Am J Physiol Regul Integr Comp Physiol* 292: R2151-2158)

Purification of Antibodies (Abs)

Anti-TrkB or anti-CO Abs from rat sera were affinity-purified on B1 or CO peptide, respectively, coupled by their N-terminus end to activated CNBr-Sepharose 4B column (Amersham Biosciences, Uppsala, Sweden) according to manufacturer's instructions. Sera diluted 2 times in PBS were loaded on the column at 4° C. The Abs were eluted with 0.2 M glycine pH 2.7, collected in tubes containing 1 M Tris buffer pH 8, subsequently dialyzed against PBS overnight at 4° C. and finally stored at −20° C.

Fab Fragment Preparation

Fab fragments were obtained by papain (Fluke) digestion of the affinity purified anti-TrkB Abs in a 1/100 ratio papain/Abs. After 8 h at 37° C. reaction was stopped by iodoacetamide 30 mM (Sigma). Fab fragments were dialysed against PBS and purified by affinity chromatography on CNBr-Sepharose 4B (GE Healthcare) coupled to TrkB peptide. Purity of the Fab was assessed by silver stained SDS-PAGE gel.

Cell Culture

Embryonic stem cells were differentiated and cultured as described by Bibel M et al., 2004, *Nat Neurosci* 7:1003-1009. PC12 cells expressing human (h) TrkB were cultured in Dulbecco's Modified Eagle Medium (DMEM) (Sigma, St. Louis, Mo., USA) containing 10% horse serum and 5% fetal calf serum (Bioconcept, Allschwil, Switzerland), 1% penicillin/streptomycin (Gibco, Grand Island, N.Y., USA) in a humidified atmosphere containing 7% $CO_2$ at 37° C.

Immunocytofluorescence

PC12 cells expressing TrkB were fixed for 15 min with 2% paraformaldehyde in PBS. Slides were saturated with PBS supplemented with 1% BSA. Anti-TrkB or anti-CO peptide Abs (7 µg/ml) were applied on cells for 1 h at RT. After 2 washes with PBS, goat anti-rat Alexafluor 594-conjugated (1/500, Molecular Probes, Junction City, Oreg., USA) was allowed to react with the fixed primary Ab for 1 h at RT. 4',6-diamidino-2-phenylindole, dihydrochloride (DAPI) (1

µg/ml, Molecular Probes) was used for nuclear staining. The same magnification (400×) and exposure time (500 ms) were used for each slide.

Immunoprecipitation

PC12 cells expressing the TrkB were lysed in cold RIPA buffer (50 mM Tris pH 8, 150 mM NaCl, 1% NP-40 0.5% sodium deoxycholate, 0.1% SDS) supplemented with anti-protease cocktail (Roche) for 1 h on ice. After a centrifugation of 30 min at 10,000×g protein concentration was determined by using BCA kit (Pierce Chemical, Rockford, Ill., USA). 100 µg of TrkB membrane preparations were incubated with 25 µg purified anti-TrkB Abs or 2.5 µg of commercial anti-TrkB Abs (sc-11, Santa Cruz) overnight at 4° C. The mixture was immunoprecipitated with 30 µl of protein G. The samples were loaded on a 10% polyacrylamide gel and transferred onto nitrocellulose membranes. The presence of TrkB was detected using anti-TrkB mAb 1/500 (BD Biosciences).

Trk B Phosphorylation Assay

PC12 cells expressing TrkB were transferred to 6-well culture plates, pretreated with poly L-lysine (Sigma), 3 days before the experiments. PC12 cells or neurons were washed for 4 h with Dulbecco's Modified Eagle Medium (Sigma-Aldrich) and preincubated for 30 min at 37° C. with 10 nM purified anti-TrkB Abs in PBS supplemented with 0.1% BSA (Sigma). Cells were then treated with increasing concentrations of BDNF ($10^{-10}$ M to $10^{-6}$ M) for 15 min at 37° C. Cells were washed with PBS, collected in tubes and the pellets were lysed with cold RIPA buffer (50 mM Tris pH 8, 150 mM NaCl, 1% NP-40 0.5% sodium deoxycholate, 0.1% SDS) supplemented with anti-protease (Roche) and anti-phosphatase (1/100, Sigma P2850 and P5726) for 1 h on ice. After a centrifugation of 30 min at 10,000×g, 15 µg of supernatants (determined by using the BCA kit, Pierce Chemical, Rockford, Ill.) were loaded on 10% polyacrylamide gel and transferred to a nitrocellulose membrane. The presence of phospho TrkB was detected using anti-phospho TrkB Abs 1/100 (Cell Signaling) and the signal was normalized using anti-TrkB mAb 1/500 (BD Biosciences). The presence of phospho PLCγ was detected by anti-phospho PLCγ Abs 1/500 (Cell Signaling) and the signal was normalized using anti-PLCγ Abs 1/2000 (Cell Signaling). Results are expressed as the percentage of maximum of the ratio between phospho and total Trk or PLCγ protein.

TrkB Internalization Assay

TrkB internalization assay was performed as described by Du et al., 2003. PC12 cells expressing TrkB were pretreated with or without 10 nM of anti-TrkB Abs during 30 min at 4° C. Then cells were stimulated with BDNF ($10^{-8}$M) for 15 min at 4° C. Cells were washed three times with cold PBS. The cell surface proteins were labeled with 0.5 mg/ml NHS-SS-biotin (Pierce Chemical Co.) in PBS containing 10 mM $Ca^{2+}$ and 10 mM $Mg^{2+}$ for 2.5 min at 37° C., and then washed extensively with ice-cold PBS. Internalization was initiated by switching to warm media (37° C.) for 30 min. The remaining, biotinylated surface proteins were debiotinylated by washing with glutathione buffer (50 mM reduced glutathione, 100 mM NaCl, 1 mg/ml BSA, 1 mg/ml glucose, and 50 mM Tris, pH 8.6) for 3 times 30 min at 4° C. The cells were washed two more additional times with PBS and harvested with the lysis buffer (see TrkB phosphorylation assay). The internalized, biotinylated proteins (50 µg) were precipitated by immobilized streptavidin, separated by SDS-PAGE, and subjected to Western blot using a monoclonal anti-TrkB Ab (1:200; Cell Signaling).

Glucose and Insulin Tolerance Test

The day before glucose or insulin tolerance test, rats were submitted to 50% food restriction. The following day rats received glucose intraperitoneal (i.p.) injection at 10 mg/kg for glucose tolerance test or insulin (0.45 U/ml at 2 ml/kg) at 9:30 a.m. Blood was collected by tail bleeding at t=0, 15, 30, 60 and 120 min after i.p. injection. Plasma glucose (RTU kit, Biomérieux, Marcy l'Etoile, France) and plasma insulin (rat insulin RIA kit Linco, St. Charles, Mo., USA) were measured. The same experiment was performed for the insulin tolerance test with an intraperitoneal (0.45 U/mL in 2 mL/kg) with a plasma glucose measurement.

Intracerebroventricular (i. c. v.) Cannulation

Male Sprague-Dawley rats (275 to 325 g) were anesthetized with isoflurane in medicinal oxygen (4% for induction and 2% for maintenance of anesthesia). A stainless steel cannula (26 gauge, 10 mm long) was implanted into the third cerebral ventricle using the following coordinates, relative to the Bregma: −2.3 mm anteroposterior, 0 mm lateral to the midline, and −7.5 mm ventral to the surface of the skull. The guide cannula was secured in place with 4 stainless steel screws and dental acrylic and cement, and a stylet was inserted to seal the cannula until use. Temgesic® (Essex Chemie AG, Lucerne, Switzerland) (0.03 mg/kg) was given subcutaneously for 2 days post-surgery. Seven days after recovery from surgery, accuracy of the cannula placement in the third ventricle was tested by measuring the dipsogenic response (immediate drinking of at least 5 ml water in 15 min) to an i.c.v. injection of 20 pmol of angiotensin II in 5 µl injection volume.

I.c.v. Injections

Purified anti-TrkB Abs were slowly (1 min) injected i.c.v. at 9:00 a.m. at a dose of 1 µg in a volume of 2 µl using a Hamilton syringe. Following the injection of rat Abs, food intake was continuously recorded during the following 3 days using an automatic food intake apparatus (TSE Systems, Bad Homburg, Germany) at one hour intervals.

Injection of Lipopolysaccharide

Lipopolysaccharide (LPS) (Sigma) was injected intraperitoneally (i.p.) at a dose of 75 µg/kg at 5:30 p.m., i.e. 30 min before the beginning of the dark phase. Food intake was continuously measured.

Manufacture of Monoclonal Antibodies

Balb/C mice were immunized with 25 µg of the free B1 peptide emulsified in complete Freund's adjuvant and injected subcutaneously (s.c.). Four weeks later a booster injection of 25 µg in incomplete Freund's adjuvant was given. Another four weeks later 10 µg peptide dissolved in NaCl 0.9% was injected i.v. three days before harvesting the spleen cells for fusion. Fusion was performed with polyethylene glycol 1500 (Sigma, Saint Louis, Mo., USA) at a ratio of 2 splenocytes for 1 SP2O myeloma cell. Hybridomas were cultivated in 96 well plates precoated with peritoneal macrophages of C57BL/6 mice 1000 cells/well. $5 \times 10^5$ cells were distributed per well in Isocoves Modified Dulbecco's Medium (IMDM) supplemented with 10% heat inactivated fetal calf serum, 200 mM glutamine, 100 mM sodium pyruvate, 1% penicillin streptomycin (Omnilab, Mettmenstetten, Switzerland), 3% Hypoxanthine, Aminopterine, Thymidine (HAT, Gibco, Lucerne, Switzerland) in a humidified incubator at 37° C. under an atmosphere of 5% $CO_2$. Secreting clones were screened by enzyme immunoassay and subcloned by limiting dilution (Oi et al., J Exp Med 1980; 151: 1260-1274).

Isolation of $V_H$ and $V_L$ Genes

Total RNA was prepared from $10^7$ freshly subcloned hybridoma cells using the RNAnow kit (Biogentex Inc., Seabrook, Tex., USA) and first strand cDNA was synthesized using iScript™ cDNA Synthesis kit (Biorad, Hercules, Calif., USA). The $V_H$ and $V_L$ chain domains were amplified by PCR using IgG primer set (Novagen, Gibbstown, N.J., USA). The 50 μl PCR mixtures contained 50 ng hybridoma cDNA, 20 pmol of each appropriate primer, 250 μM of each dNTP, 1× Taq buffer (Sigma) and 1U *Thermophilus aquaticus* (Taq) polymerase. Amplification included 50 cycles of 1.5 min at 94° C., 2.5 min at 55° C. and 3 min at 72° C. in a thermocycler (PTC-150, MJ Research, Waltham, Mass., USA). The amplified DNAs were ligated into the pGEMT vector (Promega, Madison, Wis., USA) and the recombinant plasmids purified using miniprep kit (Qiagen, Hombrechtikon, Switzerland). The DNA sequences of the cloned $V_H$ and $V_L$ inserts were determined using the ABI PRISM Cycle Sequencing kit (Applied Biosystem™, Carlsbad, Calif., USA) and M13 Forward and Reverse primers. The sequences of the V genes were determined in two independent batches of RNA preparations to ensure accuracy.

Construction of the scFv Genes scFv proteins were created by joining their $V_H$ and $V_L$ genes together by PCR splicing with overlap extensions using oligonucleotides that encoded a 15 amino-acid linker $(G_4\text{-}S)_3$ between the C-terminal of the $V_H$ and the N-terminal of the $V_L$ gene. The ends of the 1 E8a mAb variable gene were modified by PCR using specific primers from mouse IgG primer set (NOVAGEN). The scFv gene was inserted in frame with the PeIB sequence on the expression vector pET22b (EMD Biosciences, Darmstadt, Germany) between the NcoI and XhoI sites.

The invention claimed is:

1. The hybridoma cell line named 5G5D2B5 deposited at the DSMZ under the number DSM ACC3124 on Apr. 15, 2011.

2. The monoclonal antibody named 5G5D2B5, produced by the hybridoma cell line according to claim 1.

3. A fragment of the antibody of claim 2 retaining the binding specificity to B1 peptide of SEQ ID NO:2.

4. The fragment according to claim 3 which is a Fab fragment or an scFv fragment.

5. A pharmaceutical composition comprising an antibody fragment according to claim 3.

6. A method of treating anorexia or cachexia comprising administering a therapeutically efficient amount of an antibody fragment according to claim 3 to a patient in need thereof.

7. The hybridoma cell line named 6B72C5 deposited at the DSMZ under the number DSM ACC3125 on Apr. 15, 2011.

8. The monoclonal antibody named 6B72C5, produced by the hybridoma cell line according to claim 7.

9. A fragment of the antibody of claim 8 retaining the binding specificity to B1 peptide of SEQ ID NO:2.

10. The fragment according to claim 9 which is a Fab fragment or an scFv fragment.

11. A pharmaceutical composition comprising an antibody fragment according to claim 9.

12. A method of treating anorexia or cachexia comprising administering a therapeutically efficient amount of an antibody fragment according to claim 9 to a patient in need thereof.

13. An antibody or antibody fragment that binds to B1 peptide of SEQ ID NO:2 comprising light chain variables CDR L1: CRSSTGAVTTSNYAS (SEQ ID NO:9); CDR L2: GGTNNRA (SEQ ID NO:10); CDR L3: CALCYSNHLV (SEQ ID NO:11); and heavy chain variables CDR H1: SGFTFSNYAMS (SEQ ID NO:12); CDR H2: ISSGGSTYYPDSVKGR (SEQ ID NO:13); and CDR H3: CARGRGLRLRSYYYALDY (SEQ ID NO:14).

14. A pharmaceutical composition comprising an antibody or antibody fragment according to claim 13.

15. A method of treating anorexia or cachexia comprising administering a therapeutically efficient amount of an antibody or antibody fragment according to claim 13 to a patient in need thereof.

16. An antibody or antibody fragment that binds to B1 peptide of SEQ ID NO:2 comprising light chain variables CDR L1: CSLSSQHSTYTIE (SEQ ID NO:3); CDR L2: LKKDGSH (SEQ ID NO:4); CDR L3: CGVGD-TIKEQFVYV (SEQ ID NO:5); and heavy chain variables CDR H1: SGFNIKDTYMH (SEQ ID NO:6); CDR H2: IDPAHNNIKYDPKFQGK (SEQ ID NO:7); and CDR H3: CTGSLGRGDYF (SEQ ID NO:8).

17. A pharmaceutical composition comprising an antibody or antibody fragment according to claim 16.

18. A method of treating anorexia or cachexia comprising administering a therapeutically efficient amount of an antibody or antibody fragment according to claim 16 to a patient in need thereof.

* * * * *

SEQUENCE LISTING

<160> NUMBER OF SEQ ID NOS: 14

<210> SEQ ID NO 1
<211> LENGTH: 822
<212> TYPE: PRT
<213> ORGANISM: Homo sapiens

<400> SEQUENCE: 1

Met Ser Ser Trp Ile Arg Trp His Gly Pro Ala Met Ala Arg Leu Trp
1               5                   10                  15

Gly Phe Cys Trp Leu Val Val Gly Phe Trp Arg Ala Ala Phe Ala Cys
                20                  25                  30

Pro Thr Ser Cys Lys Cys Ser Ala Ser Arg Ile Trp Cys Ser Asp Pro
            35                  40                  45

Ser Pro Gly Ile Val Ala Phe Pro Arg Leu Glu Pro Asn Ser Val Asp
        50                  55                  60

Pro Glu Asn Ile Thr Glu Ile Phe Ile Ala Asn Gln Lys Arg Leu Glu
65                  70                  75                  80

Ile Ile Asn Glu Asp Asp Val Glu Ala Tyr Val Gly Leu Arg Asn Leu
                85                  90                  95

Thr Ile Val Asp Ser Gly Leu Lys Phe Val Ala His Lys Ala Phe Leu
                100                 105                 110

Lys Asn Ser Asn Leu Gln His Ile Asn Phe Thr Arg Asn Lys Leu Thr
            115                 120                 125

Ser Leu Ser Arg Lys His Phe Arg His Leu Asp Leu Ser Glu Leu Ile
        130                 135                 140

Leu Val Gly Asn Pro Phe Thr Cys Ser Cys Asp Ile Met Trp Ile Lys
145                 150                 155                 160

Thr Leu Gln Glu Ala Lys Ser Ser Pro Asp Thr Gln Asp Leu Tyr Cys
                165                 170                 175

Leu Asn Glu Ser Ser Lys Asn Ile Pro Leu Ala Asn Leu Gln Ile Pro
            180                 185                 190

Asn Cys Gly Leu Pro Ser Ala Asn Leu Ala Ala Pro Asn Leu Thr Val
        195                 200                 205

Glu Glu Gly Lys Ser Ile Thr Leu Ser Cys Ser Val Ala Gly Asp Pro
    210                 215                 220

Val Pro Asn Met Tyr Trp Asp Val Gly Asn Leu Val Ser Lys His Met
225                 230                 235                 240

Asn Glu Thr Ser His Thr Gln Gly Ser Leu Arg Ile Thr Asn Ile Ser
                245                 250                 255

Ser Asp Asp Ser Gly Lys Gln Ile Ser Cys Val Ala Glu Asn Leu Val
            260                 265                 270

```
Gly Glu Asp Gln Asp Ser Val Asn Leu Thr Val His Phe Ala Pro Thr
            275                 280                 285
Ile Thr Phe Leu Glu Ser Pro Thr Ser Asp His His Trp Cys Ile Pro
290                 295                 300
Phe Thr Val Lys Gly Asn Pro Lys Pro Ala Leu Gln Trp Phe Tyr Asn
305                 310                 315                 320
Gly Ala Ile Leu Asn Glu Ser Lys Tyr Ile Cys Thr Lys Ile His Val
            325                 330                 335
Thr Asn His Thr Glu Tyr His Gly Cys Leu Gln Leu Asp Asn Pro Thr
            340                 345                 350
His Met Asn Asn Gly Asp Tyr Thr Leu Ile Ala Lys Asn Glu Tyr Gly
            355                 360                 365
Lys Asp Glu Lys Gln Ile Ser Ala His Phe Met Gly Trp Pro Gly Ile
            370                 375                 380
Asp Asp Gly Ala Asn Pro Asn Tyr Pro Asp Val Ile Tyr Glu Asp Tyr
385                 390                 395                 400
Gly Thr Ala Ala Asn Asp Ile Gly Asp Thr Thr Asn Arg Ser Asn Glu
            405                 410                 415
Ile Pro Ser Thr Asp Val Thr Asp Lys Thr Gly Arg Glu His Leu Ser
            420                 425                 430
Val Tyr Ala Val Val Ile Ala Ser Val Val Gly Phe Cys Leu Leu
            435                 440                 445
Val Met Leu Phe Leu Leu Lys Leu Ala Arg His Ser Lys Phe Gly Met
450                 455                 460
Lys Gly Pro Ala Ser Val Ile Ser Asn Asp Asp Ser Ala Ser Pro
465                 470                 475                 480
Leu His His Ile Ser Asn Gly Ser Asn Thr Pro Ser Ser Glu Gly
            485                 490                 495
Gly Pro Asp Ala Val Ile Ile Gly Met Thr Lys Ile Pro Val Ile Glu
            500                 505                 510
Asn Pro Gln Tyr Phe Gly Ile Thr Asn Ser Gln Leu Lys Pro Asp Thr
            515                 520                 525
Phe Val Gln His Ile Lys Arg His Asn Ile Val Leu Lys Arg Glu Leu
            530                 535                 540
Gly Glu Gly Ala Phe Gly Lys Val Phe Leu Ala Glu Cys Tyr Asn Leu
545                 550                 555                 560
Cys Pro Glu Gln Asp Lys Ile Leu Val Ala Val Lys Thr Leu Lys Asp
            565                 570                 575
Ala Ser Asp Asn Ala Arg Lys Asp Phe His Arg Glu Ala Glu Leu Leu
            580                 585                 590
Thr Asn Leu Gln His Glu His Ile Val Lys Phe Tyr Gly Val Cys Val
            595                 600                 605
Glu Gly Asp Pro Leu Ile Met Val Phe Glu Tyr Met Lys His Gly Asp
610                 615                 620
Leu Asn Lys Phe Leu Arg Ala His Gly Pro Asp Ala Val Leu Met Ala
625                 630                 635                 640
Glu Gly Asn Pro Pro Thr Glu Leu Thr Gln Ser Gln Met Leu His Ile
            645                 650                 655
Ala Gln Gln Ile Ala Ala Gly Met Val Tyr Leu Ala Ser Gln His Phe
            660                 665                 670
Val His Arg Asp Leu Ala Thr Arg Asn Cys Leu Val Gly Glu Asn Leu
            675                 680                 685
```

```
Leu Val Lys Ile Gly Asp Phe Gly Met Ser Arg Asp Val Tyr Ser Thr
    690                 695                 700
Asp Tyr Tyr Arg Val Gly Gly His Thr Met Leu Pro Ile Arg Trp Met
705                 710                 715                 720
Pro Pro Glu Ser Ile Met Tyr Arg Lys Phe Thr Thr Glu Ser Asp Val
                725                 730                 735
Trp Ser Leu Gly Val Val Leu Trp Glu Ile Phe Thr Tyr Gly Lys Gln
            740                 745                 750
Pro Trp Tyr Gln Leu Ser Asn Asn Glu Val Ile Glu Cys Ile Thr Gln
        755                 760                 765
Gly Arg Val Leu Gln Arg Pro Arg Thr Cys Pro Gln Glu Val Tyr Glu
770                 775                 780
Leu Met Leu Gly Cys Trp Gln Arg Glu Pro His Met Arg Lys Asn Ile
785                 790                 795                 800
Lys Gly Ile His Thr Leu Leu Gln Asn Leu Ala Lys Ala Ser Pro Val
                805                 810                 815
Tyr Leu Asp Ile Leu Gly
            820

<210> SEQ ID NO 2
<211> LENGTH: 20
<212> TYPE: PRT
<213> ORGANISM: Homo sapiens

<400> SEQUENCE: 2

Thr Ile Thr Phe Leu Glu Ser Pro Thr Ser Asp His His Trp Cys Ile
1               5                   10                  15

Pro Phe Thr Val
            20

<210> SEQ ID NO 3
<211> LENGTH: 13
<212> TYPE: PRT
<213> ORGANISM: Rattus norvegicus

<400> SEQUENCE: 3

Cys Ser Leu Ser Ser Gln His Ser Thr Tyr Thr Ile Glu
1               5                   10

<210> SEQ ID NO 4
<211> LENGTH: 7
<212> TYPE: PRT
<213> ORGANISM: Rattus norvegicus

<400> SEQUENCE: 4

Leu Lys Lys Asp Gly Ser His
1               5

<210> SEQ ID NO 5
<211> LENGTH: 14
<212> TYPE: PRT
<213> ORGANISM: Rattus norvegicus

<400> SEQUENCE: 5

Cys Gly Val Gly Asp Thr Ile Lys Glu Gln Phe Val Tyr Val
1               5                   10

<210> SEQ ID NO 6
<211> LENGTH: 11
<212> TYPE: PRT
<213> ORGANISM: Rattus norvegicus
```

-continued

<400> SEQUENCE: 6

Ser Gly Phe Asn Ile Lys Asp Thr Tyr Met His
1               5                   10

<210> SEQ ID NO 7
<211> LENGTH: 17
<212> TYPE: PRT
<213> ORGANISM: Rattus norvegicus

<400> SEQUENCE: 7

Ile Asp Pro Ala His Asn Asn Ile Lys Tyr Asp Pro Lys Phe Gln Gly
1               5                   10                  15

Lys

<210> SEQ ID NO 8
<211> LENGTH: 11
<212> TYPE: PRT
<213> ORGANISM: Rattus norvegicus

<400> SEQUENCE: 8

Cys Thr Gly Ser Leu Gly Arg Gly Asp Tyr Phe
1               5                   10

<210> SEQ ID NO 9
<211> LENGTH: 15
<212> TYPE: PRT
<213> ORGANISM: Rattus norvegicus

<400> SEQUENCE: 9

Cys Arg Ser Ser Thr Gly Ala Val Thr Thr Ser Asn Tyr Ala Ser
1               5                   10                  15

<210> SEQ ID NO 10
<211> LENGTH: 7
<212> TYPE: PRT
<213> ORGANISM: Rattus norvegicus

<400> SEQUENCE: 10

Gly Gly Thr Asn Asn Arg Ala
1               5

<210> SEQ ID NO 11
<211> LENGTH: 10
<212> TYPE: PRT
<213> ORGANISM: Rattus norvegicus

<400> SEQUENCE: 11

Cys Ala Leu Cys Tyr Ser Asn His Leu Val
1               5                   10

<210> SEQ ID NO 12
<211> LENGTH: 11
<212> TYPE: PRT
<213> ORGANISM: Rattus norvegicus

<400> SEQUENCE: 12

Ser Gly Phe Thr Phe Ser Asn Tyr Ala Met Ser
1               5                   10

<210> SEQ ID NO 13
<211> LENGTH: 16
<212> TYPE: PRT
<213> ORGANISM: Rattus norvegicus

```
<400> SEQUENCE: 13

Ile Ser Ser Gly Gly Ser Thr Tyr Tyr Pro Asp Ser Val Lys Gly Arg
1               5                   10                  15

<210> SEQ ID NO 14
<211> LENGTH: 18
<212> TYPE: PRT
<213> ORGANISM: Rattus norvegicus

<400> SEQUENCE: 14

Cys Ala Arg Gly Arg Gly Leu Arg Leu Arg Ser Tyr Tyr Ala Leu
1               5                   10                  15

Asp Tyr
```